United States Patent
Ichiki et al.

(10) Patent No.: US 10,400,236 B2
(45) Date of Patent: Sep. 3, 2019

(54) METHOD OF MANUFACTURING PROTEIN ARRAY OR PEPTIDE ARRAY, METHOD OF IDENTIFYING FUNCTIONAL PROTEIN OR FUNCTIONAL PEPTIDE, PROTEIN ARRAY OR PEPTIDE ARRAY, AND FUNCTIONAL PROTEIN OR FUNCTIONAL PEPTIDE IDENTIFICATION KIT

(71) Applicants: THE UNIVERSITY OF TOKYO, Tokyo (JP); NIKON CORPORATION, Tokyo (JP)

(72) Inventors: Takanori Ichiki, Tokyo (JP); Shingo Ueno, Tokyo (JP); Hisao Osawa, Kashiwa (JP)

(73) Assignees: The University of Tokyo, Tokyo (JP); Nikon Corporation, Tokyo (JP)

( * ) Notice: Subject to any disclaimer, the term of this patent is extended or adjusted under 35 U.S.C. 154(b) by 0 days.

(21) Appl. No.: 15/784,031

(22) Filed: Oct. 13, 2017

(65) Prior Publication Data
US 2018/0044665 A1 Feb. 15, 2018

Related U.S. Application Data

(62) Division of application No. 14/914,373, filed as application No. PCT/JP2014/070583 on Aug. 5, 2014, now abandoned.

(30) Foreign Application Priority Data

Aug. 30, 2013 (JP) ................................. 2013-180693

(51) Int. Cl.
*C12N 15/10* (2006.01)
*C07K 17/14* (2006.01)
(Continued)

(52) U.S. Cl.
CPC ............ *C12N 15/1075* (2013.01); *C07K 1/04* (2013.01); *C07K 17/14* (2013.01); *C40B 30/04* (2013.01);
(Continued)

(58) Field of Classification Search
CPC .................. C12N 15/1075; G01N 33/6845
See application file for complete search history.

(56) References Cited

U.S. PATENT DOCUMENTS 7,674,752 B2  3/2010  He et al.
2004/0161748 A1  6/2004  He et al.
(Continued)

FOREIGN PATENT DOCUMENTS

JP  2004-506898 A  3/2004
JP  2012-70654 A  4/2012
(Continued)

OTHER PUBLICATIONS

Office Action dated Jul. 31, 2018 by the Japanese Patent Office in counterpart Japanese Patent Application No. 2015-534114, and English translation thereof.
(Continued)

*Primary Examiner* — Narayan K Bhat
(74) *Attorney, Agent, or Firm* — Finnegan, Henderson, Farabow, Garrett & Dunner LLP

(57) ABSTRACT

There is provided a method of manufacturing a protein array or peptide array suitable for an efficient screening of a functional protein or functional peptide. The method of manufacturing a protein array or peptide array includes the steps of: (a) preparing a nucleic acid immobilized on a solid support and a cell-free synthesis system in a reactor, in which a reactor array includes the reactor having a specific aperture shape and a protein capture molecule or a peptide capture molecule provided on at least a portion of wall
(Continued)

surface and bottom surface in the reactor; and (c) synthesizing a protein or peptide from the nucleic acid using the cell-free synthesis system and immobilizing the protein or peptide in the reactor.

11 Claims, 10 Drawing Sheets

Specification includes a Sequence Listing.

(51) Int. Cl.
    *C07K 1/04*     (2006.01)
    *C40B 30/04*     (2006.01)
    *G01N 33/68*     (2006.01)
(52) U.S. Cl.
    CPC ..... *G01N 33/6842* (2013.01); *G01N 33/6845* (2013.01)

(56) References Cited

U.S. PATENT DOCUMENTS

| | | |
|---|---|---|
| 2013/0237430 A1 | 9/2013 | Ichiki et al. |
| 2014/0296111 A1 | 10/2014 | Ueno et al. |

FOREIGN PATENT DOCUMENTS

| | | |
|---|---|---|
| WO | WO 02/14860 A1 | 2/2002 |
| WO | WO 2006/131687 A1 | 12/2006 |
| WO | WO 2012/026541 A1 | 3/2012 |
| WO | WO 2013/063126 A2 | 5/2013 |
| WO | WO 2013/065782 A1 | 5/2013 |

OTHER PUBLICATIONS

Requirement for Restriction/Election dated Apr. 20, 2017 in the parent U.S. Appl. No. 14/914,373.
Office Action dated Jul. 14, 2017 in the parent U.S. Appl. No. 14/914,373.
Takulapalli et al., "High Density Diffusion-Free Nanowell Arrays," 2012, J. Proteome Res., 11, 4382-4391.
Kim et al., "Ultra High Density Protein Spots Achieved by on hip Digitalized Protein Synthesis, 2013," Analyst, 138, 4663-4669, published on Jun. 19, 2013.
Moriyasu, J., et al., Intaglio printing of protein array pattern using coupled transcription-translation system (2010), p. 12-401.
Moriyasu, J., et al., Intaglio printing of protein array pattern using coupled transcription-translation system [II], (2011), p. 12-238.
International Search Report, PCT/JP2014/070583, dated Nov. 11, 2014.
Written Opinion, PCT/JP2014/070583, dated Nov. 11, 2014.
Biyani, M. et al., "Microintaglio Printing of In situ Synthesized Proteins Enables Rapid Printing of High-Density Protein Microarrays Directly from DNA Microarrays," IOP Science (2013), Retrieved from: http://iopscience.iop.or/article/10.7567/APEX.6.087001/pdf.
Biyani, M. et al., "Molecular Screening on a Chip by DNA-Displayed Protein Microarray," 15th International Conference on Miniaturized Systems for Chemistry and Life Sciences (Oct. 2-6, 2011). Retrieved from: http//www.rsc.org/images/LOC/2011/PDFs/Papers/487_0683.pdf.
Okano, T. et al., "Cell-free protein synthesis from a single copy of DNA in a glass microchamber," Lab on a Chip: Miniaturisation for Chemistry, Physics, Biology, Materials Science and Bioengineering, vol. 12, No. 15, pp. 2704-2711 (2012).
Toepke, M. et al., "PDMS absorption of small molecules and consequences in microfluidic application," Lab on a Chip: Miniaturisation for Chemistry., Physics, Biology, Materials Science and Bioengineering, vol. 6, No. 12, pp. 1484-1486 (2006).
Okano, T. et al., "Cell-free Protein Synthesis in a Microchamber Revealed the Presence of an Optimum Compartment Volume for High-order Reactions," ACS Synthetic Biology, vol. 3, No. 6, pp. 347-352 (2006).
Supplementary European Search Report issued by the European Patent Office in Application No. 14840261.3, dated Mar. 15, 2017 (10 pages).

METHOD OF MANUFACTURING PROTEIN ARRAY OR PEPTIDE ARRAY, METHOD OF IDENTIFYING FUNCTIONAL PROTEIN OR FUNCTIONAL PEPTIDE, PROTEIN ARRAY OR PEPTIDE ARRAY, AND FUNCTIONAL PROTEIN OR FUNCTIONAL PEPTIDE IDENTIFICATION KIT

CROSS-REFERENCE TO RELATED APPLICATIONS

This application is a continuation of U.S. application Ser. No. 14/914,373, filed Feb. 25, 2016, which is a 371 of PCT/JP2014/070583, filed Aug. 5, 2014, which claims priority to Japanese Patent Application 2013-180693, filed Aug. 30, 2013. The disclosure of the above-referenced applications is expressly incorporated herein by reference in its entirety.

TECHNICAL FIELD

The present invention relates to a method of manufacturing a protein array or peptide array, a method of identifying a functional protein or functional peptide, a protein array or peptide array, and a functional protein or functional peptide identification kit.

DESCRIPTION OF THE RELATED ART

New functional proteins are expected to contribute to biological applications, such as pharmaceuticals, detergents, food processing, reagents for research and development, clinical analysis, bioenergy, and biosensors.

Regarding the acquisition of new functional proteins, protein engineering techniques to design a protein from the structural information of the protein by human intelligence were mainstream techniques. However, in order to obtain a more useful function protein, it is necessary to efficiently screen proteins than techniques known in the related art, and evolutionary molecular engineering techniques repeating the random molecular structure modification and selection of proteins are expected.

For example, in the manufacturing of bioethanol, cellulose, which is a raw material, is decomposed into cellobiose, and cellobiose is further decomposed into glucose, and then ethanol is obtained by alcohol fermentation. In the decomposition process thereof, the decomposition reaction of cellobiose into glucose is slow to control the reaction rate in the entire process. Since the reaction rate in this decomposition reaction depends on oligosaccharide-degrading enzyme β-glucosidase (hereinafter, referred to as BGL), the creation of a mutant having more excellent activity has been required.

In the functional improvement of proteins, such as enzymes and antibodies, high efficiency screening using a mutant library is required. In order to efficiently perform the screening for a useful protein, a method of evaluating an enormous number of mutants simultaneously and parallelly is desired.

For such a request, there has been proposed a method of manufacturing a protein array for immobilizing a protein synthesized from DNA disposed in a well to the wall surface of the well (refer to Patented Literatures 1 and 2).

CITATION LIST

Patent Literature

[Patented Literature 1] PCT International Publication No. WO 02/014860

[Patented Literature 2] PCT International Publication No. WO 2013/063126

SUMMARY OF INVENTION

Problems to be Solved

However, the protein array proposed in Patented Literature 1 is an array of at most 1536 well formats, and has room for improvement as an array for evaluating an enormous number of mutants simultaneously and parallelly.

Further, the protein array proposed in Patented Literature 2 is difficult to recover DNA after the screening of a functional protein, and has room for improvement in the efficient screening of the functional protein.

The present invention has been made in view of the above circumstances, and an object of the present invention is to provide a method of manufacturing a protein array or peptide array suitable for efficient screening of a functional protein or functional peptide, a method of identifying a functional protein or functional peptide, a protein array or peptide array, and a functional protein or functional peptide identification kit.

Means for Solving the Problems

The present inventors have conducted intensive studies for solving the above problems. As a result, they have found that a protein or peptide is synthesized from nucleic acids immobilized on a solid support in a reactor constituting an array, and the synthesized protein or peptide is immobilized on at least a portion of the wall surface and bottom surface of the reactor, thereby solving the above problems. Embodiments of the present invention are to provide the following (1) to (7).

(1) An embodiment of the present invention is characterized in that it is a method of manufacturing a protein array or peptide array, comprising the steps of: (a) preparing a nucleic acid immobilized on a solid support and a cell-free synthesis system in a reactor, in which a reactor array includes the reactor having a specific aperture shape and a protein capture molecule or a peptide capture molecule provided on at least a portion of wall surface and bottom surface in the reactor; and (c) synthesizing a protein or peptide from the nucleic acid using the cell-free synthesis system and immobilizing the protein or peptide in the reactor.

(2) An embodiment of the present invention is characterized in that it is a method of manufacturing a protein array or peptide array, comprising the steps of: (a) preparing DNA immobilized on a solid support and a cell-free synthesis system in a reactor, in which a reactor array includes the reactor having a specific aperture shape and a nucleic acid linker having a protein linking moiety or a peptide linking moiety provided on at least a portion of wall surface and bottom surface in the reactor; and (c) transcribing mRNA from DNA using the cell-free synthesis system in the reactor, synthesizing a protein or peptide from the mRNA hybridized to the nucleic acid linker, and immobilizing the protein or peptide in the reactor.

(3) An embodiment of the present invention is characterized in that it is a protein array or peptide array, manufactured by the above method of manufacturing a protein array or a peptide array.

(4) An embodiment of the present invention is characterized in that it is a method of identifying a functional protein or functional peptide, including the step of: (d) performing a functional screening using the above protein array or peptide array to specify a reactor.

(5) An embodiment of the present invention is characterized in that it is a protein array or peptide array, comprising: a reactor array comprising a reactor having a specific aperture shape; and a nucleic acid immobilized on a solid support disposed in the reactor and a protein or peptide encoded by the nucleic acid, wherein the reactor comprises a protein capture molecule or peptide capture molecule for capturing the protein or peptide, the capture molecule being immobilized on at least a portion of wall surface and bottom surface in the reactor.

(6) An embodiment of the present invention is characterized in that it is a protein array or peptide array, comprising: a reactor array including a reactor having a specific aperture shape; and a DNA disposed in the reactor and a protein or peptide encoded by the DNA, in which the reactor includes an mRNA synthesized from the DNA immobilized on at least a portion of wall surface and bottom surface in the reactor, and a nucleic acid linker having a protein linking moiety or a peptide linking moiety capturing the protein or peptide.

(7) An embodiment of the present invention is characterized in that it is a functional protein or functional peptide identification kit, comprising: the above protein array or peptide array; and a substrate having an affinity to the solid support.

Effects of the Invention

According to the present invention, it is possible to efficiently perform the screening of a functional protein or a functional peptide.

EMBODIMENTS FOR CARRYING OUT THE INVENTION

Figure 1:
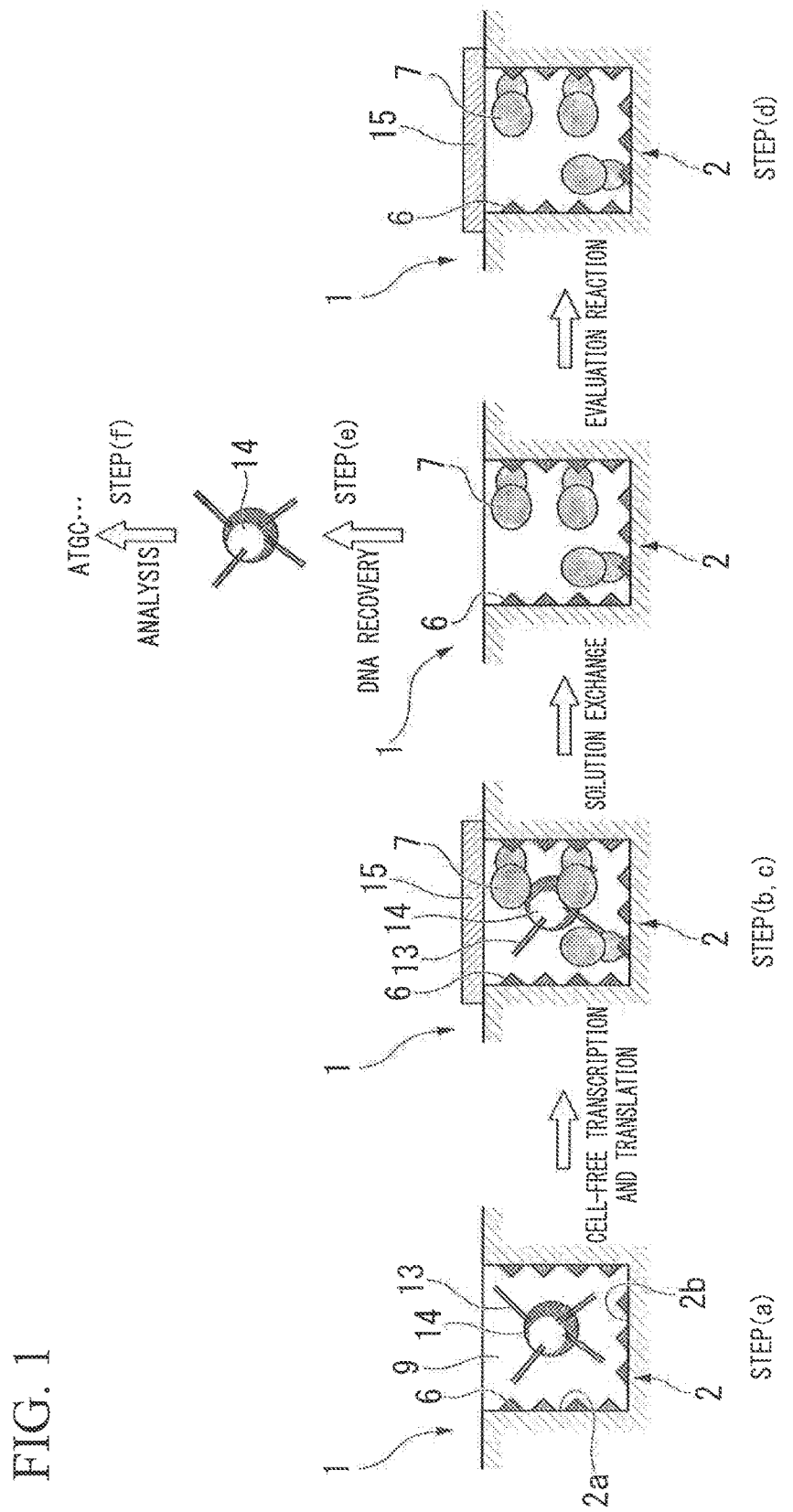
FIG. 1 A schematic view of a method of manufacturing a protein array or a peptide array and a method of identifying a functional protein or a functional peptide according to the present embodiment.

<<Method of Manufacturing Protein Array or Peptide Array>>

First Embodiment

The method of manufacturing a protein array or a peptide array according to the present embodiment comprises the steps of: (a) preparing a nucleic acid immobilized on a solid support and a cell-free synthesis system in a reactor, in which a reactor array comprises the reactor having a specific aperture shape and a protein capture molecule or a peptide capture molecule provided on at least a portion of wall surface and bottom surface in the reactor; and (c) synthesizing a protein or peptide from the nucleic acid using the cell-free synthesis system and immobilizing the protein or peptide in the reactor.

Hereinafter, the method of manufacturing a protein array or a peptide array according to the present embodiment will be described in detail with reference to FIG. 1.

In the present embodiment, in the step (a), in a reactor array 1 comprising a reactor 2 having a specific aperture shape and a protein capture molecule or peptide capture molecule 6 provided on at least a portion of wall surface 2a and bottom surface 2b in the reactor 2, a nucleic acid immobilized on a solid support and a cell-free synthesis system 9 are added into the reactor 2.

The material used for the reactor array 1 is preferably quartz, glass, or a polymer material. The polymer material is more preferably an elastomer material, such as polydimethylsiloxane (Hereinafter, referred to as PDMS), for the purpose of suppressing leakage.

It is preferable that the reactor array 1 comprises a plurality of reactors 2. The number of the reactors 2 is preferably 10000 to 500000000, and more preferably 10000000 to 50000000.

In the present embodiment, since the reactor array 1 comprising the reactor 2 having a wall is individually used, it is not necessary to take an alignment at the time of superimposing a substrate on a reactor, which has been required at the time of manufacturing a protein array from a DNA array or at the time of performing a functional screening using a protein array.

The shape of the reactor 2, for example, is a well shape, a minute recess, or a groove. The bottom surface of the reactor 2, for example, is a circle or a square. The diameter or one side of the bottom surface is preferably 1 µm to 200 µm, more preferably 1 µm to 50 µm, and particularly preferably 1 µm to 5 µm. The distance between centers of the plurality of reactors 2 is preferably 1.5 µm to 500 µm, more preferably 1.5 µm to 150 µm, and particularly preferably 1.5 µm to 15 µm.

Further, the depth of the reactor 2 is preferably 1 µm to 200 µm, more preferably 1 µm to 50 µm, and particularly preferably 1 µm to 5 µm.

Further, the hydrophilic treatment of the reactor 2 may be carried out.

In the step (a), the nucleic acid added into the reactor 2 is not particularly limited as long as it encodes a protein or a peptide. Examples of the nucleic acid include DNA and RNA, and, from the viewpoint of ease of handling, DNA is preferable.

From the viewpoint of analyzing the base sequence of the nucleic acid corresponding to the reactor 2 specified by the later step (d) in the <<method of identifying a functional protein or function peptide>>, the DNA is configured such that the position information of the nucleic acids is specified in the reactor array 1. In the present embodiment, DNA 13 is immobilized on a solid support. Further, for example, the nucleic acid immobilized on the solid support is one type of nucleic acid per the one solid support.

In the immobilization of DNA, in addition to a method of using an avidin-biotin bond, a method of modifying DNA with a functional group, such as an amino group, an aldehyde group, and an SH group, and surface-treating a solid support with a silane coupling agent having an amino group, an aldehyde group, an epoxy group, or the like can be used. Particularly, the method of using an avidin-biotin bond is preferable.

The solid support is preferably a bead from the viewpoint of recovering DNA later, and is more preferably a magnetic bead 14 from the viewpoint of being possible to be arranged in the reactor 2 in the reactor array 1 in a short period of time.

In the present embodiment, when a magnetic bead is used as the solid support, it is preferable that a magnetic plate is provided under a substrate material used in the reactor array 1.

When the reactor array 1 having such a configuration is used, the magnetic bead 14 can be easily and reliably disposed in the reactor 2. For example, a magnet is provided under the substrate material, and a dispersion obtained by dispersing the magnetic beads 14 immobilizing the DNA 13 is dropped onto the substrate material. When the magnetic beads are attracted into the reactor 12 by the action of magnetic force caused by the magnet and the magnetic plate, the magnetic beads are easily arranged. In addition, when the magnetic beads 14 are dispersed by appropriately moving the magnet in a direction parallel to a substrate, the filling rate of the magnetic beads 14 into the reactor 2 is improved. The intensity of an electric field applied to the substrate for arranging the magnetic beads 14 by the magnet is preferably 100 gauss to 10000 gauss in order to obtain desired effects.

Further, since the magnetization of the magnetic plate remains even after the magnet is removed, the magnetic beads 14 can continue to hold stable arrangement.

As the material of such a magnetic plate, nickel, a nickel alloy, iron, and an iron alloy can be appropriately used. In the present embodiment, it is preferable to use a magnetic material having large residual magnetization.

The filling rate of the magnetic beads 14 in the reactor 2 depends on the diameter or one side of the reactor 2.

From the viewpoint of filling rate, it is preferable that the diameter or one side of the reactor 2 is slightly larger than that the diameter or one side of the magnetic bead 14, and it is more preferable that the diameter or one side of the reactor 2 is 1 to 2 times larger than the diameter or one side of the magnetic bead 14.

Further, in order to fill one reactor 2 with one magnetic bead 14, it is more preferable that the depth of the reactor 2 is 1 to 2 times larger than the diameter of the magnetic bead 14.

Meanwhile, as an example, one type of nucleic acid is immobilized per one solid support, and a plurality of types of nucleic acids are not immobilized on one solid support. In this case, one type of nucleic acid is provided to one reactor, and one type of protein is synthesized.

As a mixture of a plurality of types of DNA, such as a DNA library, a mutant DNA library is preferable.

Examples of the mutant DNA library include libraries using error-prone PCR, libraries using gene assembly mutagenesis, libraries using random insertion and deletion mutagenesis, libraries using DNA shuffling, a library using family shuffling, libraries using staggered extension process in vitro recombination, ITCHY hybrid protein libraries, SCRATCHY hybrid protein libraries, and libraries using sequence homology-independent protein recombination.

In the present embodiment, the reactor array 1 comprises a protein capture molecule or peptide capture molecule 6 provided on at least a portion of the wall surface 2a and bottom surface 2b in the reactor 2.

As the protein capture molecule or peptide capture molecule 6, a molecule having an affinity to an amino acid sequence existing in a protein or peptide 7 is exemplified. Examples of the molecule include: maltose; guanine nucleotide; metal ions, such as nickel ions and cobalt ions; and antigens.

Figure 2:
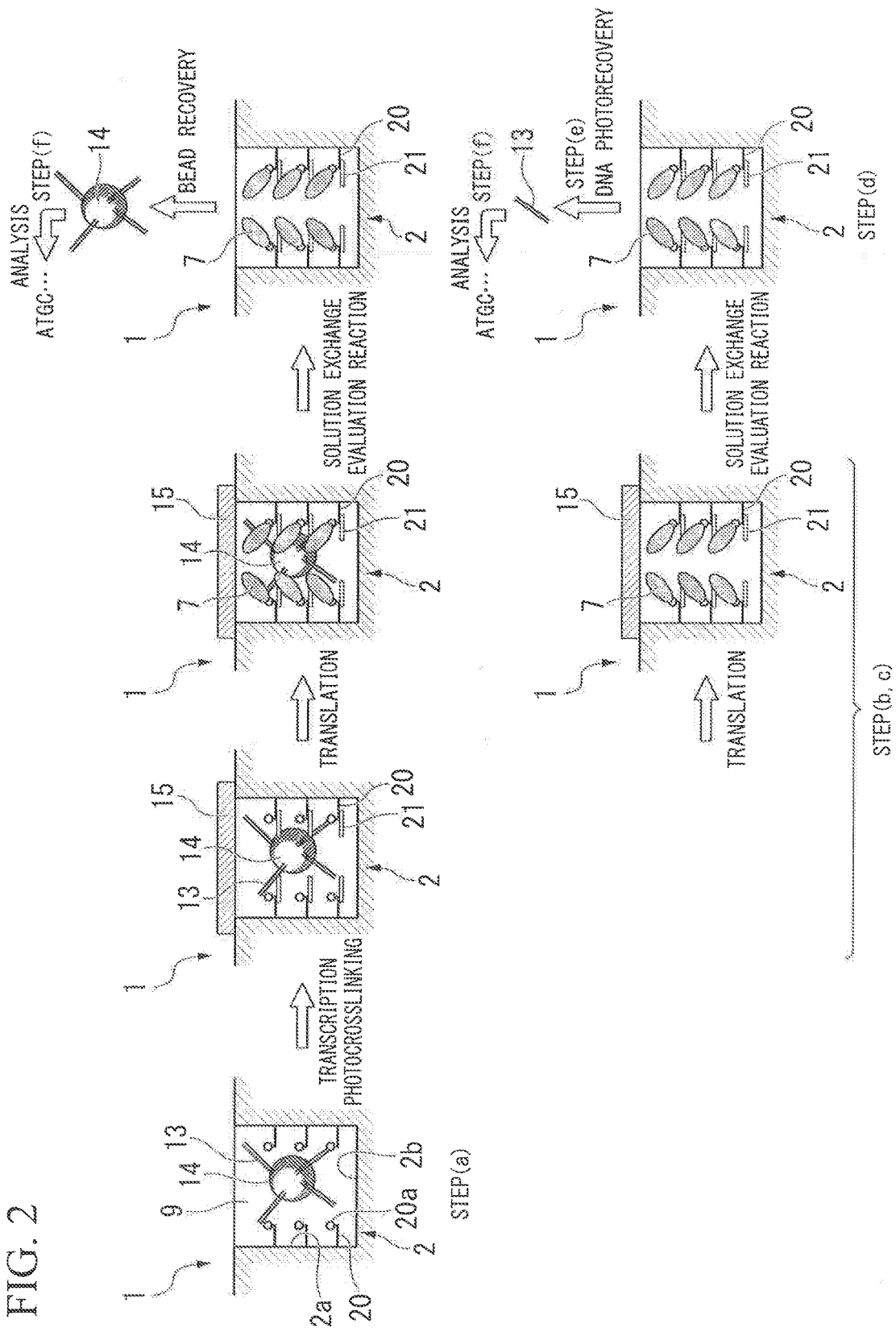
FIG. 2 A schematic view of method of a manufacturing a protein array or a peptide array and a method of identifying a functional protein or a functional peptide according to the present embodiment.

In addition, as the protein capture molecule or peptide capture molecule 6, a nucleic acid linker may be used. The nucleic acid linker includes a protein linking moiety or peptide linking moiety. The protein linking moiety or peptide linking moiety is typically puromycin (refer to Japanese Unexamined Patent Application, First Publication No. 2008-116218). As an example of the nucleic acid linker, a puromycin linker is exemplified. Puromycin is a protein synthesis inhibitor having a structure similar to the 3' terminal of aminoacyl-tRNA. As the linking moiety of a protein, any material can be used as long as it has a function to bind specifically to the C-terminal of the protein or peptide in extension. As the linking moiety, a puromycin derivative, such as 3'-N-aminoacyl puromycin aminonucleoside (PANS-amino acid) and 3'-N-aminoacyl adenosine aminonucleoside (AANS-amino acid), can be used. As shown in FIG. 2, the puromycin linker 20 includes a sequence hybrolyzable to a RNA transcribed from DNA 13, and a puromycin derivative 20a capturing the protein or peptide 7.

When the protein or peptide 7 contains polyhistidine having an affinity to metal ions, such as nickel ions and cobalt ions, a hexamer or higher thereof is preferably used as the polyhistidine. In order to contain the polyhistidine in the protein or peptide, it is preferable to previously add a base sequence encoding the polyhistidine to the terminal of DNA by PCR or the like.

The aperture shape of the reactor 2 is not limited, but is preferably a shape capable of filling the reactor 2 with at least one bead. Examples of the aperture shape of the reactor 2 may include a circular shape, a tetragonal shape, a hexagonal shape, a line shape, and the like.

In the present embodiment, it is preferable that a step (b) of sealing the reactor 2 is performed between the above step (a) and the later step (c).

As shown in FIG. 1, as an example of the step (b), a step of superimposing a substrate 15 on the reactor array 1 is exemplified. In addition, the reactor 2 may be sealed using oil or the like instead of the substrate 15.

Examples of the substrate 15 used in the step (b) include a glass substrate, a silicon substrate, a polymer substrate, and a metal substrate. The glass substrate is preferably a glass substrate coated with PDMS. At the time of sealing the reactor 2, for example, the reactor 2 is sealed using a press machine.

In addition, a glass substrate coated with PDMS in the middle stage of cross-linking may be used. Since the PDMS in the middle stage of cross-linking has adhesiveness, when the glass substrate coated with this PDMS is superimposed on the reactor array 1, the DNA immobilized on the solid support in the reactor 2 is intaglio-printed on the PDMS. Thus, the nucleic acid corresponding to the protein or peptide 7 synthesized and immobilized in the later step (c) can be printed on the PDMS without changing position information.

The step (c) is a step of synthesizing the protein or peptide 7 from a nucleic acid using a cell-free synthesis system 9 in the reactor 2 and immobilizing the protein or peptide 7 in the reactor 2.

The cell-free synthesis system 9 refers to a protein translation system composed of components having synthesis ability of proteins extracted from appropriate cells. This system contains elements necessary for translation, such as ribosome, a translation initiation factor, a translation elongation factor, a dissociation factor, and an aminoacyl-tRNA synthetase. Examples of such a protein translation system include an *E. coli* extract, a rabbit reticulocyte extract, and a wheat germ extract.

Moreover, as the cell-free synthesis system, a reconstruction type cell-free protein synthesis system including only the refined elements in the elements necessary for translation is exemplified. The reconstruction type cell-free protein synthesis system can improve translation efficiency because it can easily prevent the contamination of nuclease and protease compared to when a known cell extract is used.

When such a system is used, a protein or peptide is prepared in the reactor 2.

When the nucleic acid used in the cell-free synthesis system 9 is DNA 13 in the step (c), the step (c) comprises a step of synthesizing RNA from the DNA 13 using the cell-free synthesis system. The RNA is obtained by performing a transcription by a RNA polymerase from the immobilized DNA 13 encoding the protein or peptide to be screened. An example of the RNA polymerase includes a T7RNA polymerase.

For convenience, a system in which transcription and translation are coupled may be used.

As shown in FIG. 2, when the puromycin linker 20 is used as the protein capture molecule or peptide capture molecule, the RNA 21 synthesized from the DNA 13 is hybridized with a sequence in the puromycin linker 20.

When the puromycin linker 20 has a reversible photoligating base, the puromycin linker 20 is immobilized in the reactor 2 by light irradiation.

In the step (c), following the synthesis of the protein or peptide 7, the immobilization of the protein or peptide 7 into the reactor 2 is performed.

For example, in the step (a), a necessary reagent or material (nucleic acid) is added to the reactor 2 of the reactor array 1, and then, in the step (b), the reactor array 1 is sealed to be a sealed state. In the step (c), as soon as the reagent is mixed, a series of transcription/translation reactions of DNA→RNA→protein or peptide proceeds, and the translated protein or peptide 7 is bonded to the protein or peptide capture molecule 6 immobilized on a portion of the wall surface and bottom surface in the reactor.

After the immobilization of the protein or peptide 7 into the reactor 2, it is preferable to release the sealed state of the reactor 2 by removing the substrate 15 or oil.

Through the steps (a) to (c), it is preferable that the reactor array 1 in which the protein or peptide 7 is immobilized is cleaned with PBS or the like.

According to the method of manufacturing a protein or peptide array according to the present embodiment, when the nucleic acid immobilized on the solid support is used, it is possible to identify the protein or peptide 7 immobilized in the reactor of the manufactured protein array or peptide array, and thus it is not required to previously obtain the information of the nucleic acid disposed in the reactor.

Second Embodiment

The method of manufacturing a protein array or a peptide array according to the present embodiment comprises the steps of: (a) preparing DNA immobilized on a solid support and a cell-free synthesis system in a reactor, in which a reactor array comprises the reactor having a specific aperture shape and a nucleic acid linker having a protein linking moiety or a peptide linking moiety provided on at least a portion of wall surface and bottom surface in the reactor; and (c) transcribing mRNA from DNA using the cell-free synthesis system in the reactor, synthesizing a protein or peptide from the mRNA hybridized to the nucleic acid linker, and immobilizing the protein or peptide in the reactor.

Hereinafter, the method of manufacturing a protein array or a peptide array according to the present embodiment will be described in detail with reference to FIG. 2. In FIG. 2, in the same components as those shown in the schematic view of FIG. 1, the description thereof will be omitted with the same reference numerals.

In the step (a) according to the present embodiment, a nucleic acid linker having a protein linking moiety or a peptide linking moiety (refer to Japanese Unexamined Patent Application, First Publication No. 2008-116218) is used instead of the protein capture molecule or peptide capture molecule that has been described in the first embodiment. As an example of the nucleic acid linker includes a puromycin linker.

As shown in FIG. 2, the puromycin linker 20 includes a sequence hybridizable to the RNA 21 transcribed from the DNA 13, and a puromycin derivative 20a capturing the protein or peptide 7.

Further, in the step (a) according to the present embodiment, the DNA immobilized on the solid support is used.

Even in the present embodiment, it is preferable that a step (b) of sealing the reactor 2 is performed between the above step (a) and the later step (c).

As shown in FIG. 2, as an example of the step (b), a step of superimposing a substrate 15 on the reactor array 1 is exemplified. In addition, the reactor 2 may be sealed using oil or the like instead of the substrate 15.

The step (c) is a step of transcribing mRNA from the nucleic acid using the cell-free synthesis system 9 in the reactor 2, synthesizing a protein or peptide 7 from the mRNA hybridized to the nucleic acid linker, and immobilizing the protein or peptide 7 in the reactor 2.

In the step (c), the nucleic acid used in the cell-free synthesis system 9 is DNA 13. The step (c) includes a step of transcribing RNA 21 from the DNA 13 using a RNA polymerase in a cell-free transcription system or a cell-free transcription and translation system. The RNA 21 is obtained by performing a transcription from the DNA 13 by the RNA polymerase. An example of the RNA polymerase includes a T7RNA polymerase.

Next, the RNA 21 synthesized from the DNA 13 is hybridized with a sequence in the puromycin linker 20.

When the puromycin linker 20 has a reversible photoligating base, it is preferable that a puromycin linker 20-RNA 21 complex is immobilized in the reactor 2 by light irradiation.

Next, similarly to the step (c) in the first embodiment, a protein or peptide 7 is synthesized using the cell-free translation system from the puromycin linker 20-RNA 21 complex, and the synthesized protein or peptide 7 is bonded to the puromycin linker 20 immobilized on at least a portion of the wall surface 2a and bottom surface 2b in the reactor 2, so as to immobilize a puromycin linker 20-RNA 21-protein or peptide 7 complex in the reactor 2.

After the immobilization of the protein or peptide 7 into the reactor 2, it is preferable to release the sealed state of the reactor 2 by removing the substrate 15 or oil.

After going through the steps (a) to (c), it is preferable that the reactor array 1 in which the protein or peptide 7 is immobilized is cleaned with PBS or the like. According to the present embodiment, similarly to the first embodiment, it is not required to previously obtain the information of the nucleic acid disposed in the reactor.

Third Embodiment

The method of manufacturing a protein array or a peptide array according to the present embodiment comprises the steps of: (a) preparing DNA and a cell-free synthesis system in a reactor, in which a reactor array comprises the reactor having a specific aperture shape and a nucleic acid linker having a protein linking moiety or a peptide linking moiety provided on at least a portion of wall surface and bottom surface in the reactor; and (c) transcribing mRNA from DNA using the cell-free synthesis system in the reactor, synthesizing a protein or peptide from the mRNA hybridized to the nucleic acid linker, and immobilizing the protein or peptide in the reactor.

Figure 3:
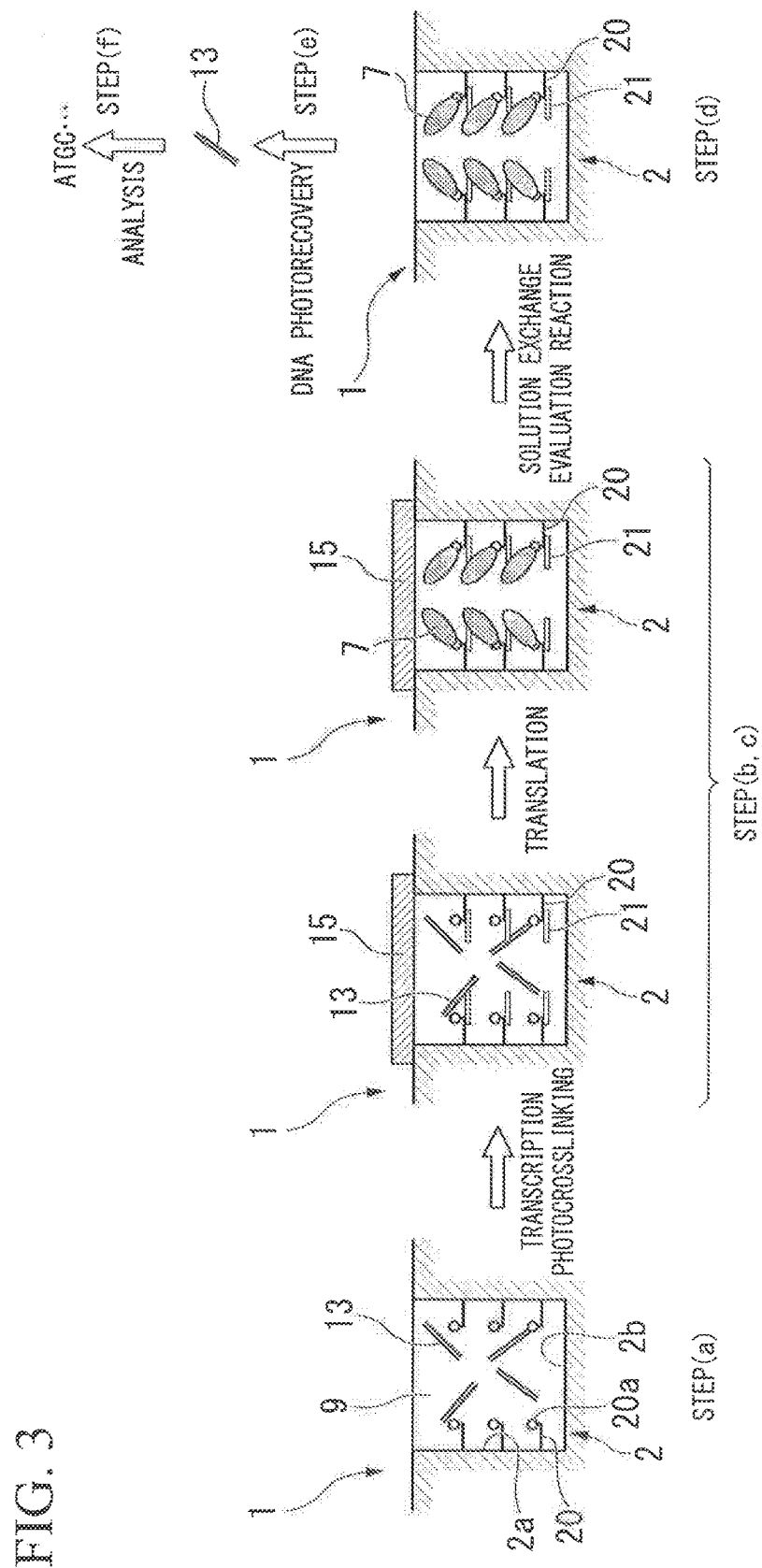
FIG. 3 A schematic view of method of a manufacturing a protein array or a peptide array and a method of identifying a functional protein or a functional peptide according to the present embodiment.

Hereinafter, the method of manufacturing a protein array or a peptide array according to the present embodiment will be described in detail with reference to FIG. 3. In FIG. 3, in the same components as those shown in the schematic views of FIGS. 1 and 2, the description thereof will be omitted with the same reference numerals.

In the step (a) according to the present embodiment, DNA not immobilized in a solid support is used instead of the DNA immobilized on the solid support, which has been described in the second embodiment.

The method of providing the DNA in the reactor is not limited to the method using the solid support, and includes a method of making DNA into one molecule per well by limiting dilution and distributing the DNA in the reactor.

According to the method of manufacturing a protein array or a peptide array according to the present embodiment, a nucleic acid and a protein or peptide can be immobilized in the reactor by using only the puromycin linker 20 without using the protein or peptide capture molecule 6 and the magnetic bead 14.

In addition, similarly to the first and second embodiments, it is not required to previously obtain the information of the nucleic acid disposed in the reactor.

<<Method of Identifying Functional Protein or Functional Peptide>>

The method of identifying functional protein or functional peptide comprises the step of: (d) performing a functional screening using the protein array or peptide array manufactured by the aforementioned manufacturing method to specify a reactor.

First Embodiment

Hereinafter, the method of identifying functional protein or functional peptide according to the present embodiment will be described in detail with reference to FIG. 1.

In the present embodiment, the step (d) is a step of performing a functional screening of the protein or peptide 7 immobilized in the reactor 2 using the protein array or peptide array manufactured by the aforementioned manufacturing method according to the first embodiment to specify a reactor.

The functional screening method is not particularly limited as long as a reactor containing a protein having desired characteristics is specified from the reactor on the reactor array.

As an example, it is preferable to fill the reactor 2 with a protein function evaluation solution by removing the cell-free protein synthesis system 9 in the reactor 2 and performing cleaning while retaining the protein or peptide 7 and a nucleic acid in the reactor 2.

Next, it preferable to specify a reactor, in which a protein or peptide having an aimed function is immobilized, by sealing the reactor with the substrate 15 or oil to make each reactor independent and performing a protein function evaluation reaction.

For example, when the protein to be screened is an enzyme, as the functional screening, an enzyme activity measurement system is exemplified. As a specific method, there is exemplified a method of measuring the activity of the protein on the reactor array by adding a solution necessary for measuring the activity of a protein (enzyme activity measurement system) into the reactor 2 and causing an enzyme reaction.

For example, when the protein to be screened is an antibody, as the functional screening, an antigen binding activity measurement system is exemplified.

As the method of measuring enzyme activity or binding activity, a well known method is used. Examples thereof include a fluorescence resonance energy transfer method (FRET method), an evanescent field molecular imaging method, a fluorescence imaging analysis method, an enzyme-linked immunosorbent assay (ELISA), a fluorescence depolarization method, a fluorescence correlation spectroscopy, and a surface plasmon resonance method.

In the present embodiment, it is preferable that a step (e) of recovering a nucleic acid in the reactor 12 is further performed before the step (d). As the recovering method, there is exemplified a method of preparing a reactor array having the same sequence as the reactor array 1 to relocate the DNA immobilized in the magnetic bead without changing the position information in the reactor array.

With the step (e) in the method, the protein or peptide 7 immobilized in the reactor 2 specified after the functional screening in the step (d) can be identified, and thus it is not required to previously obtain the information of the nucleic acid disposed in the reactor 2.

Further, even from the view point of removing contaminants other than the protein or peptide 7 immobilized in the reactor 2 to improve the accuracy of the functional screening according to the step (d), it is preferable for the present embodiment to have the step (e) of recovering a nucleic acid before the step (d).

The step (e) may be a step of superimposing a substrate having an affinity to a magnetic bead on the reactor array in the step (b) to print a nucleic acid on the substrate. As an example, there is exemplified a step of superimposing a glass substrate coated with PDMS in the middle stage of cross-linking on the reactor array 1 in the step (b) to print a nucleic acid on the PDMS.

With the step (e) in the method, the recovered nucleic acid can be reused.

Next, it is preferable in the present embodiment that a step (f) of analyzing a base sequence of a nucleic acid corresponding to the reactor specified in the step (d) is further performed. As the method of analyzing the base sequence, there is exemplified a well known method of amplifying the recovered nucleic acid by PCR or the like and using a DNA sequencer.

Further, instead of the step (f), the identification of the protein or peptide may be performed by peptide-decomposing the protein or peptide immobilized in the reactor using a protease and analyzing the decomposed peptide.

Second Embodiment

Hereinafter, the method of identifying functional protein or functional peptide according to the present embodiment will be described in detail with reference to FIG. 2.

In the present embodiment, the step (d) is a step of performing a functional screening of the protein or peptide 7 immobilized in the reactor 2 using the protein array or peptide array manufactured by the aforementioned manufacturing method according to the second embodiment to specify a reactor.

Even in the present embodiment, it is preferable that a step (e) of recovering a nucleic acid in the reactor 2 is further performed before the step (d). As the recovering method, when the puromycin linker 20 has a reversible photoligating base, there is exemplified a method of recovering a nucleic acid by cleaving the reversible photoligating base by light irradiation and dissociating a nucleic acid from the reactor 2, in addition to the aforementioned method of relocating the DNA immobilized in the magnetic bead.

Since other steps are similar to those in the first embodiment, descriptions thereof will be omitted.

Third Embodiment

Hereinafter, the method of identifying functional protein or functional peptide according to the present embodiment will be described in detail with reference to FIG. 3.

In the present embodiment, the step (d) is a step of performing a functional screening of the protein or peptide 7 immobilized in the reactor 2 using the protein array or peptide array manufactured by the aforementioned manufacturing method according to the third embodiment to specify a reactor.

Even in the present embodiment, it is preferable that a step (e) of recovering a nucleic acid in the reactor 2 is further performed before the step (d). As the recovering method, when the puromycin linker 20 has a reversible photoligating base, there is exemplified a method of recovering a nucleic acid by cleaving the reversible photoligating base by light irradiation and dissociating a nucleic acid from the reactor 2.

Since other steps are similar to those in the first and second embodiments, descriptions thereof will be omitted.

In a known method of identifying functional protein or functional peptide, since an array having no wall is individually used, an additional reactor array is required at the time of functional screening of the synthesized protein or peptide. In contrast, according to the method of identifying functional protein or functional peptide according to the present embodiment, since a reactor array comprising reactors having a wall is used, the function and sequence of the protein or peptide can be specified by one reactor array. Further, it is not necessary to take an alignment at the time of superimposing a substrate on a reactor, which has been required at the time of manufacturing a protein array from a DNA array or at the time of performing a functional screening using a protein array.

<<Protein Array or Peptide Array>>

First Embodiment

The protein array or peptide array according to the present embodiment comprises: a reactor array comprising a reactor having a specific aperture shape; and a nucleic acid immobilized on a solid support disposed in the reactor and a protein or peptide encoded by the nucleic acid.

The reactor comprises a protein capture molecule or peptide capture molecule for capturing the protein or peptide, the capture molecule being immobilized on at least a portion of the wall surface and bottom surface in the reactor.

As described in the first embodiment of the <<method of manufacturing a protein array or peptide array>>, the protein array or peptide array of the present embodiment is a protein array or peptide array in which a nucleic acid is immobilized on a solid support. The nucleic acid is preferably a nucleic acid immobilized on a magnetic bead (refer to FIG. 1).

Second Embodiment

The protein array or peptide array according to the present embodiment comprises: a reactor array comprising a reactor having a specific aperture shape; and DNA immobilized on a solid support disposed in the reactor and a protein or peptide encoded by the DNA.

The reactor comprises an mRNA synthesized from the DNA immobilized on at least a portion of wall surface and bottom surface in the reactor, and a nucleic acid linker having a protein linking moiety or a peptide linking moiety capturing the protein or peptide.

As described in the second embodiment of the <<method of manufacturing a protein array or peptide array>>, in the protein array or peptide array of the present embodiment, the nucleic acid linker having a protein linking moiety or a peptide linking moiety is used instead of the protein capture molecule or peptide capture molecule that has been described in the first embodiment (refer to FIG. 2).

Third Embodiment

The protein array or peptide array according to the present embodiment comprises: a reactor array comprising a reactor having a specific aperture shape; and DNA disposed in the reactor and a protein or peptide encoded by the DNA.

The reactor comprises an mRNA synthesized from the DNA immobilized on at least a portion of wall surface and bottom surface in the reactor, and a nucleic acid linker having a protein linking moiety or a peptide linking moiety capturing the protein or peptide.

As described in the third embodiment of the <<method of manufacturing a protein array or peptide array>>, in the protein array or peptide array of the present embodiment, the DNA not immobilized on the solid support is used instead of the DNA immobilized on the solid support, which has been described in the second embodiment (refer to FIG. 3).

<<Functional Protein or Functional Peptide Identification Kit>>

The functional protein or functional peptide identification kit according to the present embodiment comprises: the aforementioned <<protein array or peptide array>> of the first embodiment; and a substrate having an affinity to the solid support.

As described in the first embodiment of the <<method of identifying a functional protein or peptide>>, when the substrate having an affinity to the solid support is superimposed on the reactor array, a nucleic acid can be printed on the substrate.

According to the protein array or peptide array and the functional protein or functional peptide identification kit according to the present embodiment, the protein or peptide having a desired function can be rapidly identified, and thus they can be suitably used in the evolutionary molecular engineering applications.

Hereinafter, the present invention will be described by the following Examples. However, the present invention is not limited to these Examples.

EXAMPLES

[Fabrication of Quartz Glass Reactor]

Quartz glass was dipped into a mixed solution of concentrated sulfuric acid (15.5%) and hydrogen peroxide water (15.5%), and left at 200° C. for 15 minutes to clean the quartz glass with SPM. The cleaned quartz glass was rinsed with ultrapure water, and was then dried with nitrogen blow (refer to FIG. 4 (a)).

Figure 4:
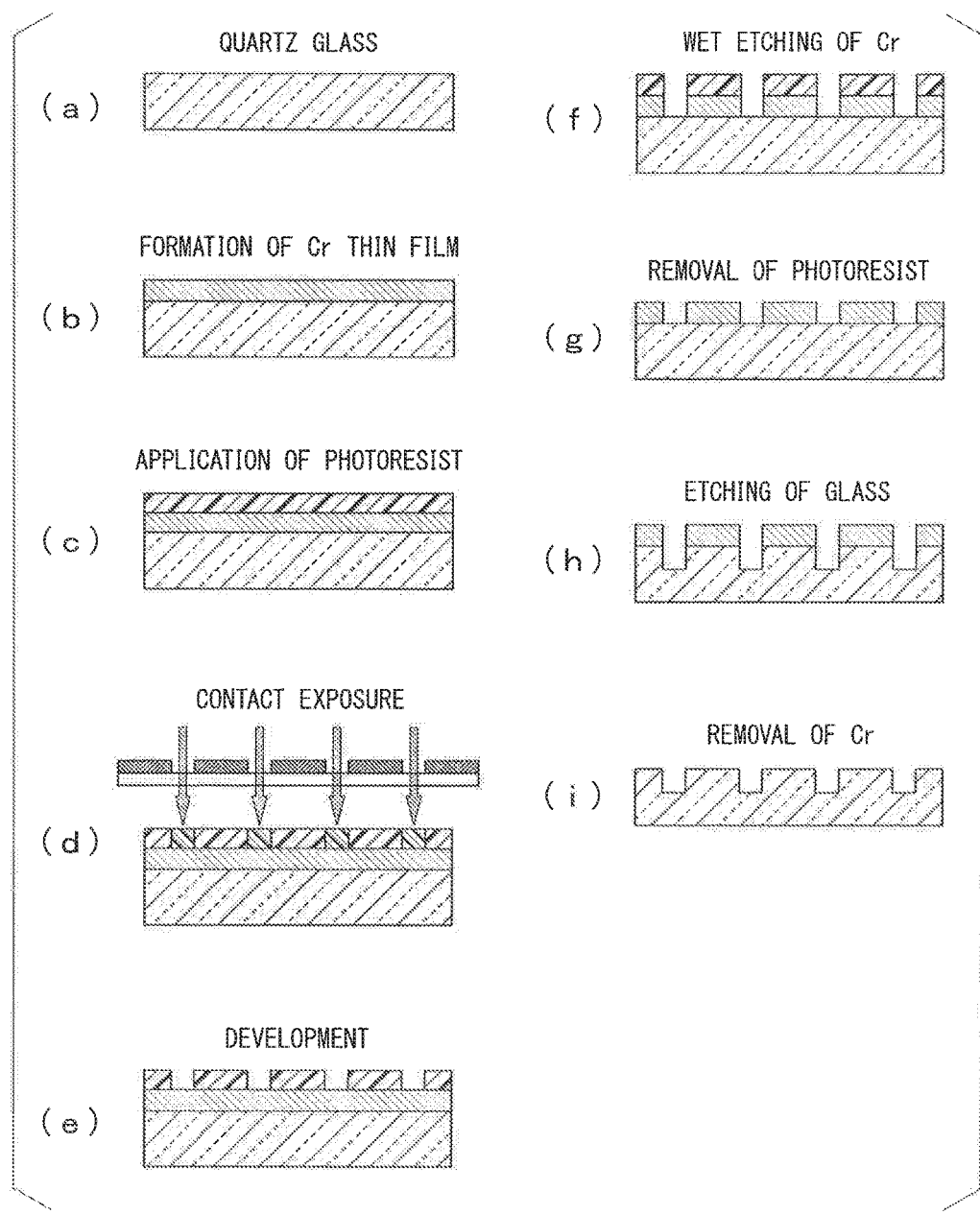
FIG. 4 A schematic view of a method of fabricating a quartz glass reactor according to Examples.

Cr was sputtered onto the quartz glass using a sputtering apparatus (Canon ANELVA SPF-430H) under Ar flow to form a thin film having a thickness of about 4 µm on the quartz glass (refer to FIG. 4 (b)).

Next, positive type photoresist AZP 1350 was applied onto the Cr thin film by spin coating, and prebaked at 100° C. for 90 seconds to form a photoresist film (refer to FIG. 4 (c)).

Next, UV exposure was carried out through a mask pattern using an ultraviolet exposure apparatus (Double-View Mask Aligner PEM-800, union) (refer to FIG. 4 (d)).

Next, development was carried out for 60 seconds using an AZ Developer, cleaning with ultrapure water was carried out, drying with $N_2$ was carried out, and then post-baking was carried out at 120° C. for 2 minutes to develop a pattern (refer to FIG. 4 (e)).

Next, pattern etching of the Cr thin film was carried out using a Cr etching solution (diammonium cerium nitrate 65.8 g, perchloric acid 17.2 ml, and ultrapure water 400 ml) (refer to FIG. 4 (f)). The pattern-etched Cr thin film was dipped into ultrapure water, and then dried with nitrogen blow.

Next, after dipping into acetone, ultrasonic cleaning was carried out for 5 minutes to remove the photoresist, and drying with nitrogen blow was carried out (refer to FIG. 4 (g)).

Next, the quartz glass was dry-etched to a depth of 60 µm using $C_4F_8/SF_6$ plasma (refer to FIG. 4 (h)).

Next, the dry-etched quartz glass was dipped into a Cr etching solution for 240 minutes, further dipped into a mixed solution of concentrated sulfuric acid (46.5%) and hydrogen peroxide water (15.5%), and left at 200° C. for 15 minutes to remove the Cr thin film, and then rinsed with ultrapure water, so as to fabricate a quartz glass reactor having a depth of 60 µm and a diameter of 140 µm (refer to FIG. 4 (i)).

[Ni-NTA Modification of Quartz Glass Reactor]

The quartz glass reactor cleaned with SPM was dipped into a 1% 3-aminopropyltriethoxysilane (hereinafter, also referred to as APTES) aqueous solution, and a reaction was performed at 90° C. for 60 minutes. After cleaning was carried out with ethanol and ultrapure water, curing was carried out at 110° C. for 1 minute, so as to modify the quartz glass reactor with an amino group (refer to step (B1) of FIG. 5).

Figure 5:
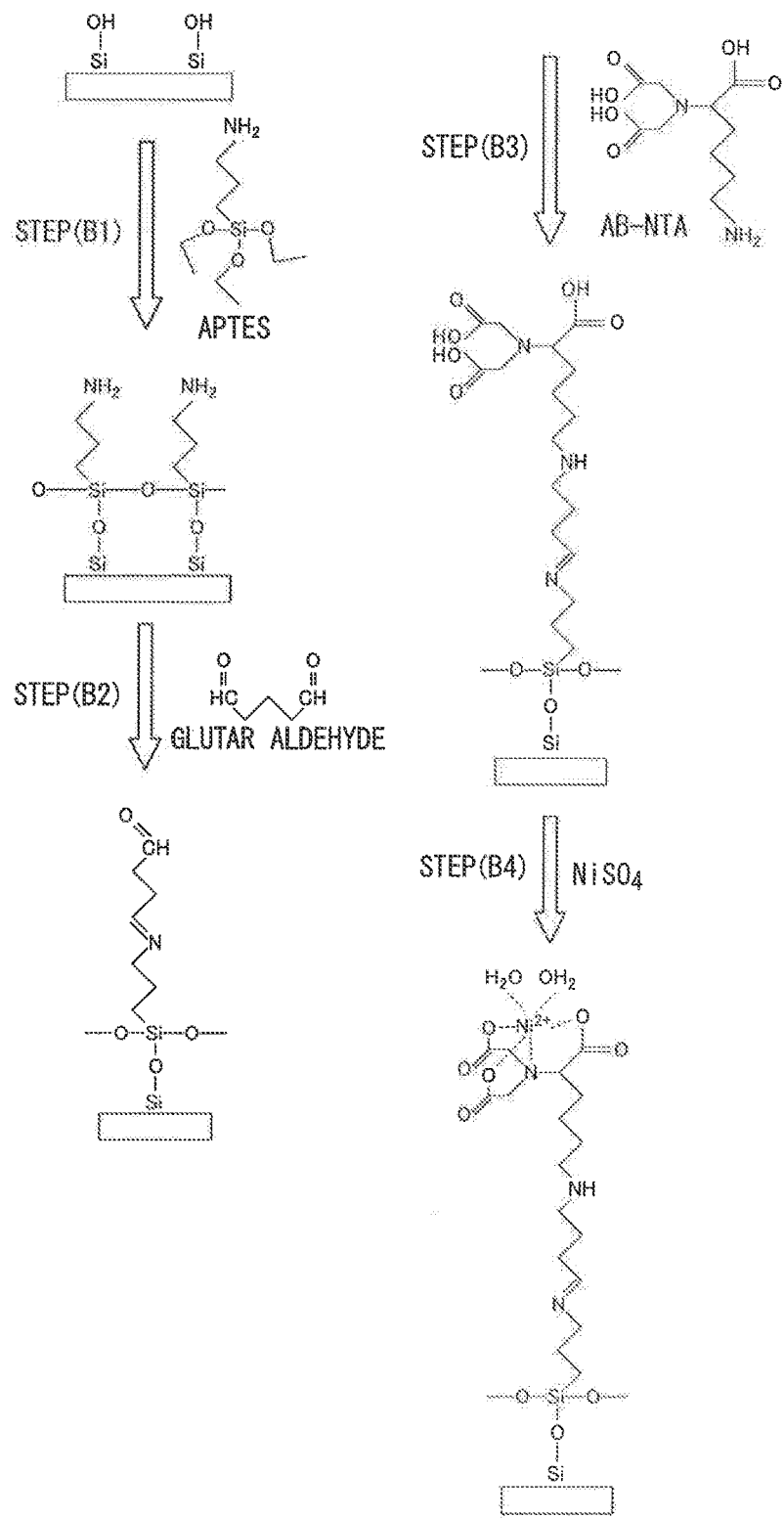
FIG. 5 A schematic view of a method of fabricating a Ni-NTA-modified quartz glass reactor according to Examples.

Next, the quartz glass reactor was dipped into a 12.5% glutaraldehyde aqueous solution at 60° C. for 60 minutes, so as to modify the quartz glass reactor with aldehyde (refer to step (B2) of FIG. 5).

Next, the quartz glass reactor was dipped into a 2 mg/ml N-(5-Amino-1-carboxypentyl)iminodiacetic acid (AB-NTA) at 60° C. for 60 minutes, so as to modify the quartz glass reactor with NTA (refer to step (B3) of FIG. 5).

Next, the quartz glass reactor was dipped into a 14 mg/ml L-Lysine at room temperature for 60 minutes, so as to block the unreacted aldehyde group.

Next, the quartz glass reactor was dipped into a 10 mg/ml $NiSO_4.6H_2O$ for 60 minutes to add Ni ion, cleaned with ultrapure water, and then dried with nitrogen blow (refer to step (B4) of FIG. 5).

[Fabricating of Cell-Free Transcription and Translation Solution]

20 ng of DNA (1687 bp) encoding BGL of SEQ ID NO. 1 and His Tag, 5 µl of Fluorotect (Promega K.K.), and 50 µl of a cell-free transcription and translation system (TNT (registered trademark) Coupled Wheatgerm Extract System, Promega KK.) were mixed to obtain a cell-free transcription and translation solution.

[Synthesis and Immobilization of BGL]

50 µl of the cell-free transcription and translation solution was dropped onto the Ni-NTA-modified quartz glass reactor, and a PDMS (Dow Corning Toray Co., Ltd.) coated glass was pressure-bonded to the dropping surface thereof at 30° C. for 2 hours.

Figure 6:
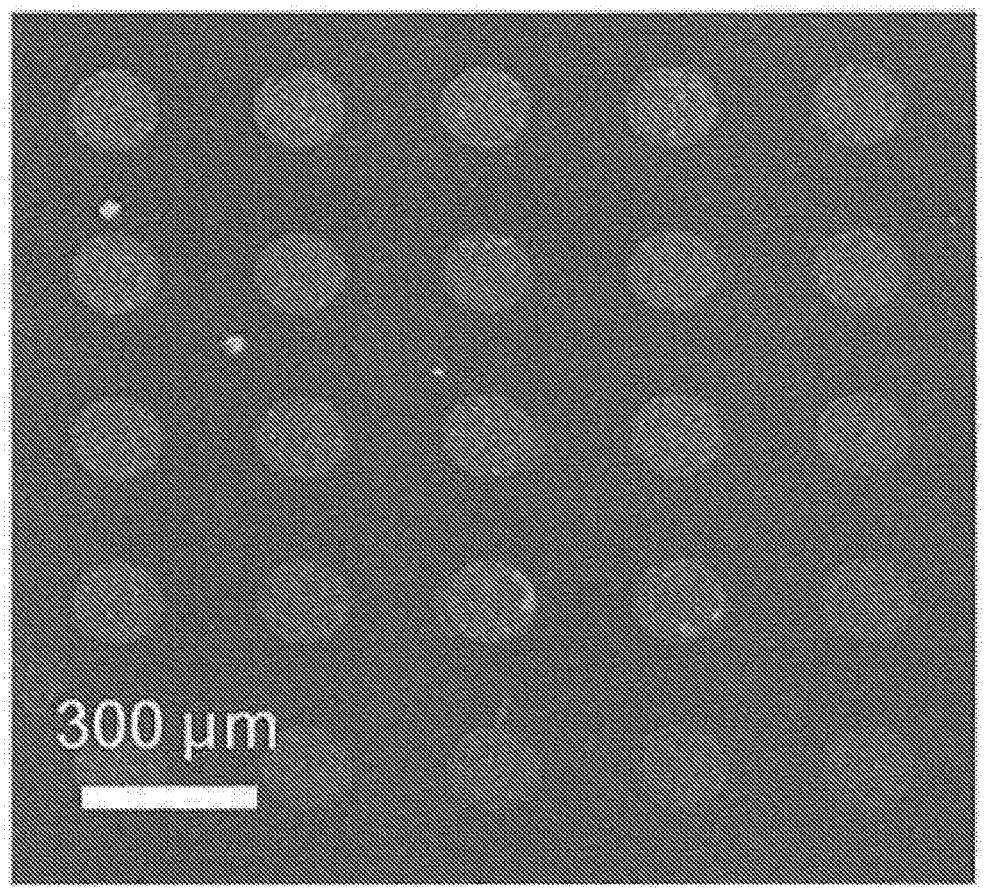
FIG. 6 A view showing the confocal microscopic image of a BGL protein array according to Examples.

Next, the PDMS-coated glass was removed, and the quartz glass reactor having this reactor was cleaned with a phosphate buffer containing 0.1% (v/v) of Tween 20 for 5 minutes. 1×PBS was dropped onto the quartz glass reactor after the cleaning, and a cover glass was placed thereon, and confocal laser scanning microscopy observation (Ex: 488 nm, Em: 515BP30 nm) was carried out. The confocal laser scanning microscopy observation (Ex: 488 nm, Em: 515BP30 nm) is shown in FIG. 6. As shown in FIG. 6, the immobilization of BGL onto the quartz glass reactor was confirmed.

Next, the PBS on the quartz glass reactor was removed by nitrogen blow, a resolfin-labeled glucose (2.5 µM resolfin-β glucose) aqueous solution, as a substrate, was dropped onto the quartz glass reactor, and a PDMS-coated glass substrate was pressed from the top surface thereof, thereby sealing the reactor with a solution.

The resultant was maintained at 30° C., and confocal laser scanning microscopy observation (Ex: 561 nm, Em: 590BP40 nm) was carried out over time.

Figure 7:
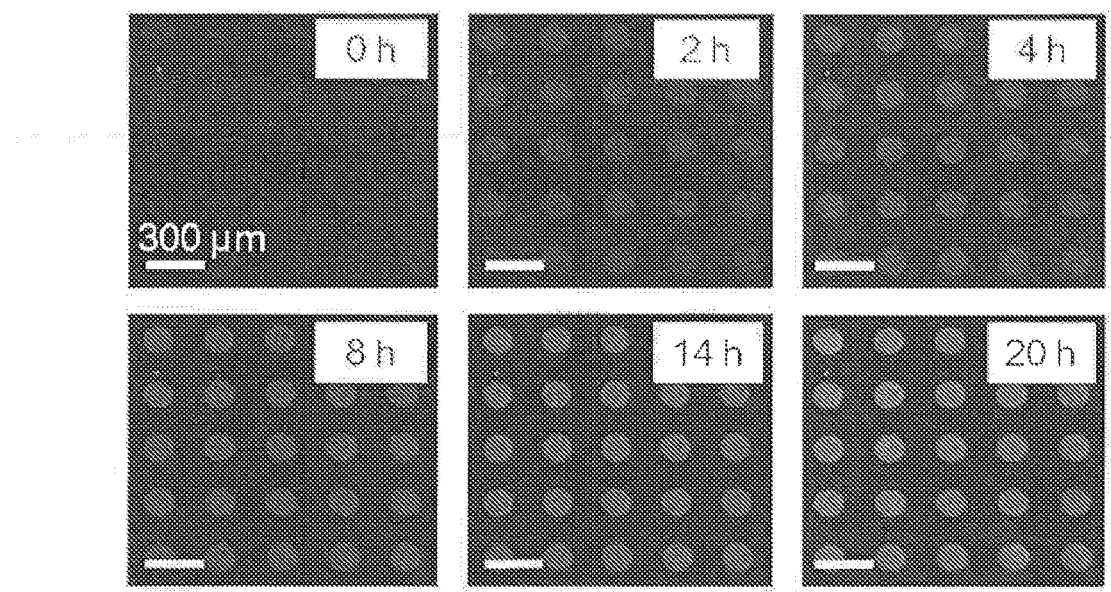
FIG. 7 A view showing the results of enzymatic reaction of the BGL protein array according to Examples.

The confocal laser scanning microscopy observation image after enzymatic reaction is shown in FIG. 7. The fluorescence resulting from the enzymatic reaction in the reactor in which the immobilization of BGL shown in FIG. 6 was confirmed was observed in a time-dependent manner.

Figure 8:
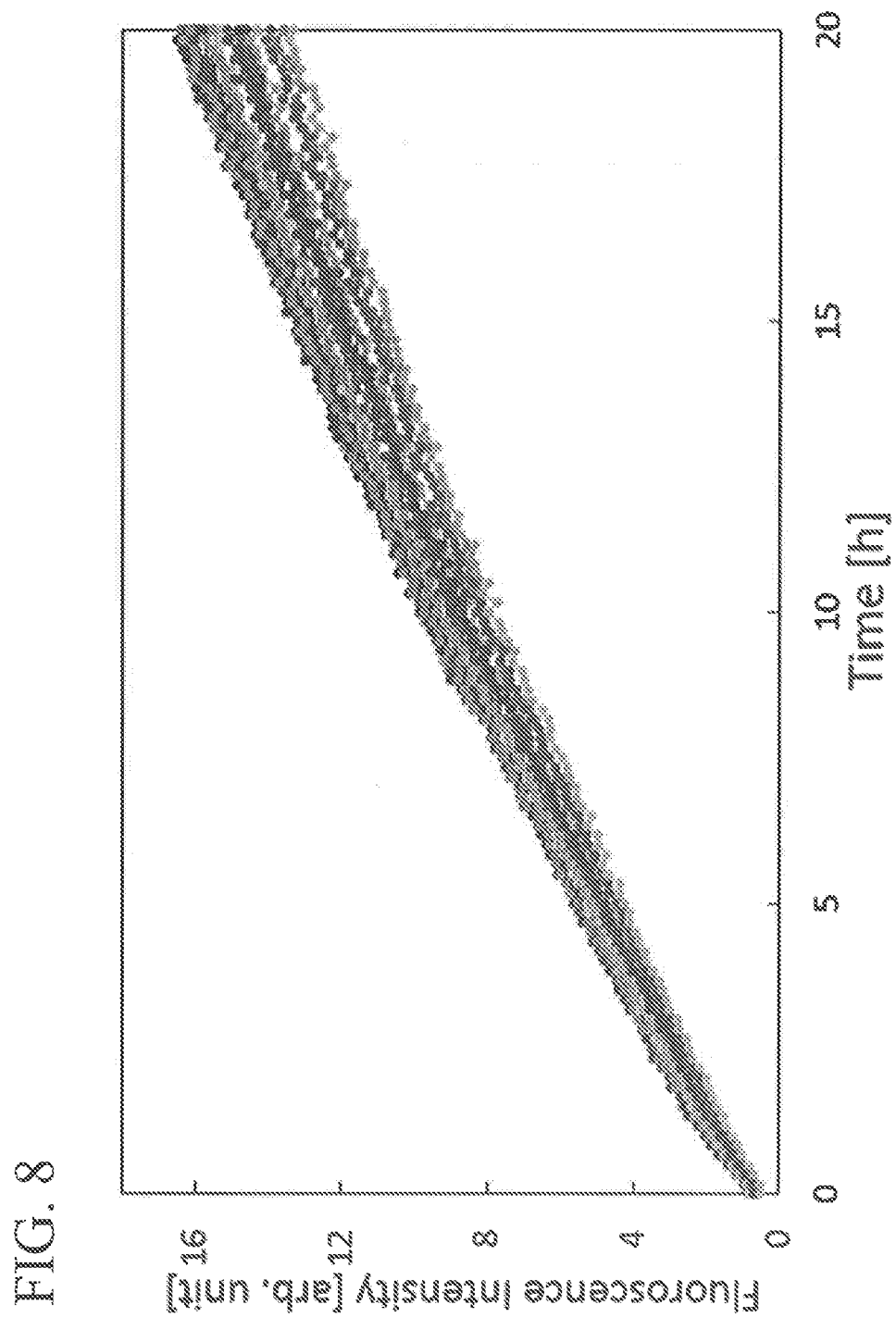
FIG. 8 A view showing the results of enzymatic reaction of the BGL protein array in each reactor according to Examples.

Further, similarly, the results of the relationship between the enzymatic reaction time and the fluorescence intensity resulting from the decomposition of the substrate in each reactor of the quartz glass reactor immobilizing the BGL are shown in FIG. 8.

As shown in FIG. 8, it was observed that, in the glass microwell mold in which BGL was immobilized, the increase in fluorescence intensity depends on time.

From these results, it was confirmed that the immobilized BGL has evaluable enzyme activity.

[Recovery of Magnetic Bead in Glass Reactor Using PDMS Sheet]

Figure 9:
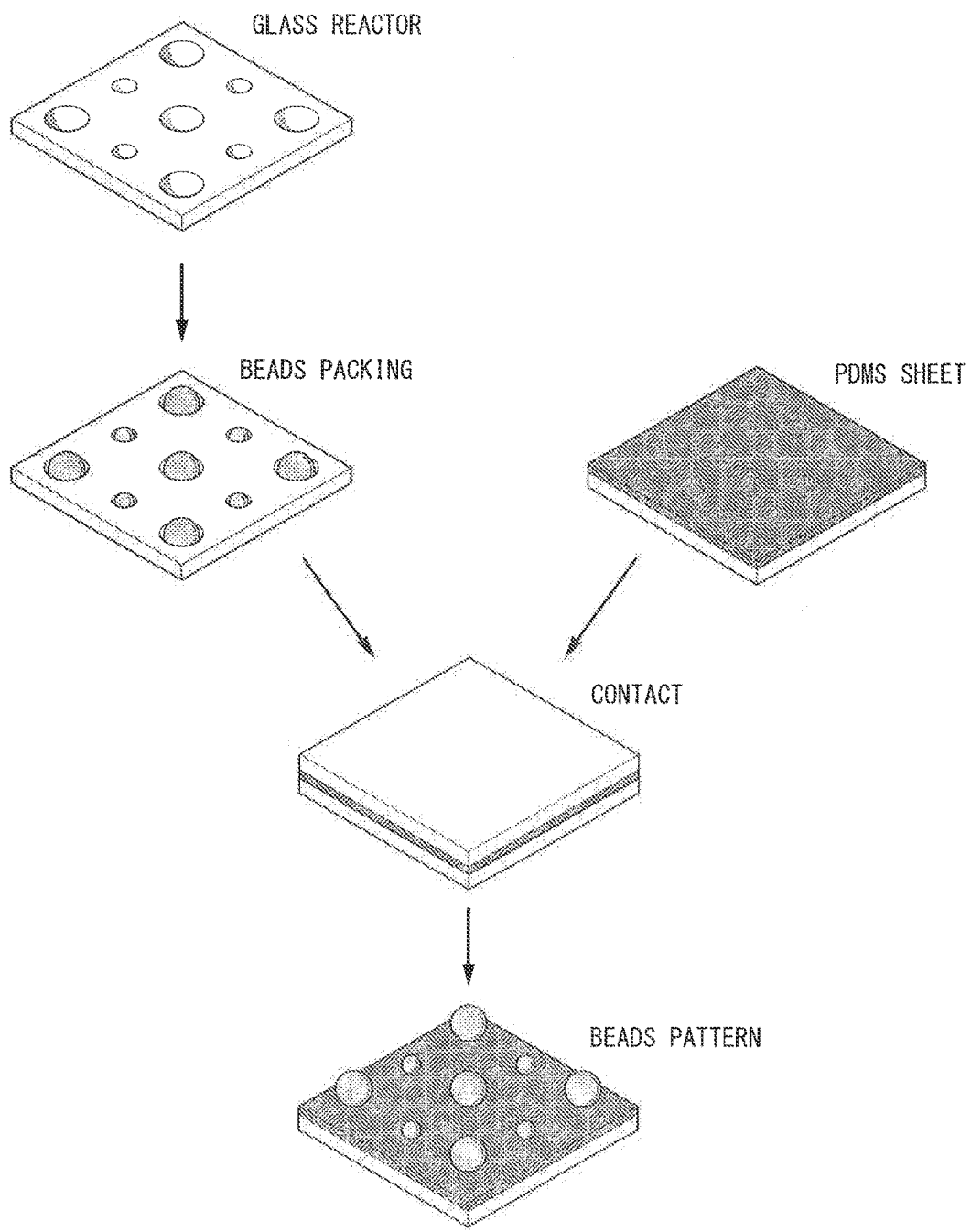
FIG. 9 A schematic view of a method of recovering magnetic beads in the glass reactor using a PDMS sheet according to Examples.

A magnetic bead was disposed in a glass reactor. Next, a PDMS (Dow Corning Toray Co., Ltd.) coated glass in the middle state of crosslinking was superimposed on the glass reactor such that the surface of PDMS comes into contact with the glass reactor. Next, the PDMS (Dow Corning Toray Co., Ltd.) coated glass was stripped from the glass reactor (refer to FIG. 9).

Figure 10:
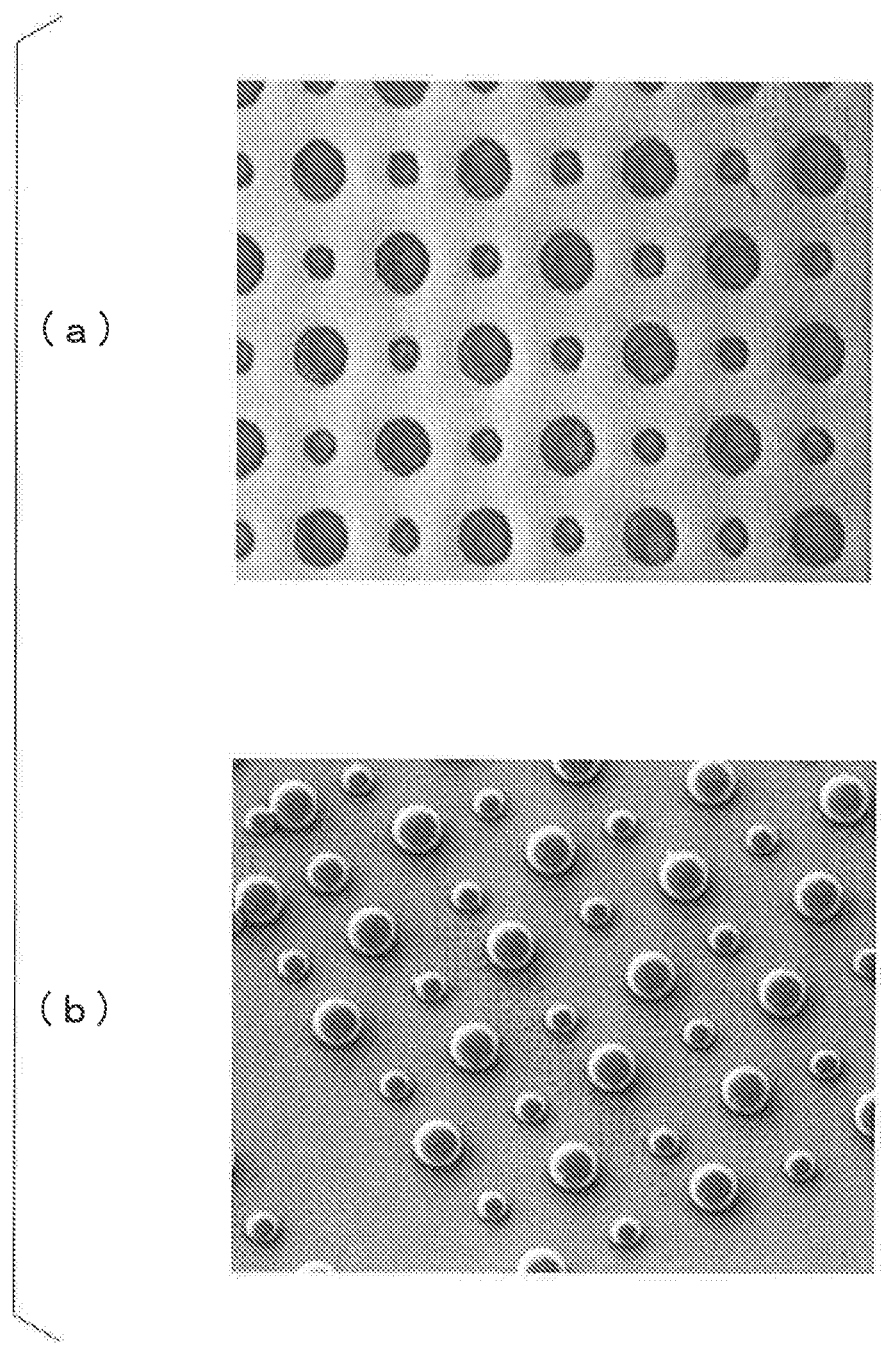
FIG. 10 A view showing the microscopic images of the magnetic beads recovered by the recovering method using the PDMS sheet on the PDMS sheet according to Examples.

The results thereof are shown in FIG. 10. (a) of FIG. 10 shows a microscope image of the glass reactor, and (b) of FIG. 10 shows a microscope image of the PDMS: It was confirmed that the magnetic bead in the glass reactor was lost as shown in (a) of FIG. 10, whereas the magnetic bead on the PDMS was recovered in correspondence with the glass reactor as shown in (b) of FIG. 10. As shown in FIG. 10, when a reactor array having a plurality of reactors is used, magnetic beads are arranged on the PDMS in correspondence with the arrangement of the reactor array. From this, the position relationship between the nucleic acid immobilized on the magnetic bead on the PDMS and the protein immobilized in the reactor can be confirmed (addressed). In addition, the magnetic bead on the PDMS can be reused.

REFERENCE SIGNS LIST

1: reactor array, 2: reactor, 2a: wall surface, 2b: bottom surface, 6: protein capture molecule or peptide capture molecule, 7: protein or peptide, 9: cell-free protein synthesis system, 13: DNA, 14: magnetic bead, 15: substrate, 20: puromycin linker, 20a: puromycin derivative, 21: RNA

SEQUENCE LISTING

<110> The University of Tokyo
<110> NIKON CORPORATION
<120> method for producing protein array or peptide array, method for screening functional protein or peptide, protein array or peptide array, and identification kit of functional protein or peptide.

<130>    PC18755

<160>    1

<210>    1

<211>    1687

<212>    DNA

<213>    Artificial Sequence

<220>

<223>    Description of Artificial Sequence: HisBGL

<400>    1

SEQ ID NO 1
gatcccgcga aattaatacg actcactata ggggaagtat ttttacaaca attaccaaca        60
acaacaacaa acaacaacaa cattacattt tacattctac aactacaagc caccatgtct       120
gcgtccgccg ctcctccaaa caagctccct gcagactttc tatgggcctt cgcaactgcg       180
agcttccaga ttgaaggcgc aactgacgtg gacggacgtg gcaagtccat ttgggacgac       240
ttctcgaaaa tacctggcaa gacgctcgac ggaaagaacg gagatgtcgc gaccgactct       300
tacaaccgct ggcgagaaga cgtcgacctg ctcgtccagt acggcgtgaa gagctaccgc       360
ttctccatct cctggtctcg tatcattccc ctcggaggcc ggaacgaccc agtaaacgag       420
gccggaatta aattrtactc ggatctcatt gatgcgctgc tcgagcgggg catcgtgccc       480
tttgtgactc tctaccactg ggarctcccg caggccctgc acgaccggta ccttggctgg       540
ctgaacaagg acgagatcgt ccaggactat gttcgctacg cggggtctg cttcgagcgt       600 tttggcgatc gagtaaaaca ctggttgacg atgaacgagc cgtggtgcat ctctattctg       660
gggtacggcc gcggggtgtt cgcgcctggc cggtcaagtg accgcatgcg ctcgccagag       720
ggtgattcct cgacagaacc ttggatcgtc ggccacagtg tgatcctggc ccatgcgtac       780
gcggtcaagc tctaccgcga gcagttcaag gcgaacaggg gcggccagat cggcatcacc       840
ctcaacggcg actgggccat gccgtacgac gacagttcgc aaaacattga ggctgctcag       900
cacgcactgg atgttgccat cggttggttc gcggaccgca tttacctcgg ccaatacccg       960
gcgtatatga aagagatgct gggcgacagg cttccggagt ttaccccgga ggaactcgct      1020
gtcgtcaagg ggtcgtcgga cttctatggc atgaacacgt acaccacgaa cctctgcaag      1080

-continued

| | |
|---|---|
| gctggtggtg aagacgagtt ccaagggaac gtcgaataca ccttcactcg ccccgacggc | 1140 |
| acgcagctcg gcactgctgc ccactgctcc tggctgcagg attacgcgcc gggcttccgc | 1200 |
| gacttgctca actacctgta caaacgttac cgcaaaccca tctacgtgac cgagaacggg | 1260 |
| ttcgcggtga aggatgagaa ctccaagccg ctcgaggaag ccctcaagga tgacgaccgc | 1320 |
| gtgcactact accagggtgt gaccgactcc ctgcttgcgg ccgtgaagga ggacggcgtt | 1380 |
| gatgtccggg gctactttgg ctggagtctt ctcgacaact tcgaatgggc ggacgggtac | 1440 |
| atcacccgct tcggtgtcac ctatgtcgac tacgacaccc aaaagcggta ccrgaaggac | 1500 |
| tcgggcaagt tcctctcaca gtggttccca gcgcacatcg cggagattga gggacgccat | 1560 |
| catcatcatc atcatggcct gaacgacatc ttcgaggctc agaaaatcga atggcacgaa | 1620 |
| tgaaagcttg cggccgcact cgagcaccac caccaccacc actgagatcc ggctgctaac | 1680 |
| aaagccc | 1687 |

SEQUENCE LISTING

<160> NUMBER OF SEQ ID NOS: 1

<210> SEQ ID NO 1
<211> LENGTH: 1687
<212> TYPE: DNA
<213> ORGANISM: Artificial Sequence
<220> FEATURE:
<223> OTHER INFORMATION: Description of Artificial Sequence:HisBGL

<400> SEQUENCE: 1

| | |
|---|---|
| gatcccgcga aattaatacg actcactata ggggaagtat ttttacaaca attaccaaca | 60 |
| acaacaacaa acaacaacaa cattacattt tacattctac aactacaagc caccatgtct | 120 |
| gcgtccgccg ctcctccaaa caagctccct gcagactttc tatggggctt cgcaactgcg | 180 |
| agcttccaga ttgaaggcgc aactgacgtg gacggacgtg gcaagtccat ttgggacgac | 240 |
| ttctcgaaaa tacctggcaa gacgctcgac ggaaagaacg gagatgtcgc gaccgactct | 300 |
| tacaaccgct ggcgagaaga cgtcgacctg ctcgtccagt acggcgtgaa gagctaccgc | 360 |
| ttctccatct cctggtctcg tatcattccc ctcggaggcc ggaacgaccc agtaaacgag | 420 |
| gccggaatta aattctactc ggatctcatt gatgcgctgc tcgagcgggg catcgtgccc | 480 |
| tttgtgactc tctaccactg ggacctcccg caggccctgc acgaccggta ccttggctgg | 540 |
| ctgaacaagg acgagatcgt ccaggactat gttcgctacg cggggggtctg cttcgagcgt | 600 |
| tttggcgatc gagtaaaaca ctggttgacg atgaacgagc cgtggtgcat ctctattctg | 660 |
| gggtacggcc gcggggtgtt cgcgcctggc cggtcaagtg accgcatgcg ctcgccagag | 720 |
| ggtgattcct cgacagaacc ttggatcgtc ggccacagtg tgatcctggc ccatgcgtac | 780 |
| gcggtcaagc tctaccgcga gcagttcaag gcgaacaggg gcggcagat cggcatcacc | 840 |
| ctcaacggcg actgggccat gccgtacgac gacagtccgc aaaacattga ggctgctcag | 900 |
| cacgcactgg atgttgccat cggttggttc gcggacccca tttacctcgg ccaatacccg | 960 |
| gcgtatatga aagagatgct gggcgacagg cttccggagt ttaccccgga ggaactcgct | 1020 |
| gtcgtcaagg gtcgtcgga cttctatggc atgaacacgt acaccacgaa cctctgcaag | 1080 |
| gctggtggtg aagacgagtt ccaagggaac gtcgaataca ccttcactcg ccccgacggc | 1140 |
| acgcagctcg gcactgctgc ccactgctcc tggctgcagg attacgcgcc gggcttccgc | 1200 |
| gacttgctca actacctgta caaacgttac cgcaaaccca tctacgtgac cgagaacggg | 1260 |

```
ttcgcggtga aggatgagaa ctccaagccg ctcgaggaag ccctcaagga tgacgaccgc    1320
gtgcactact accagggtgt gaccgactcc ctgcttgcgg ccgtgaagga ggacggcgtt    1380
gatgtccggg gctactttgg ctggagtctt ctcgacaact tcgaatgggc ggacgggtac    1440
atcacccgct tcggtgtcac ctatgtcgac tacgacaccc aaaagcggta cccgaaggac    1500
tcgggcaagt tcctctcaca gtggttccca gcgcacatcg cggagattga gggacgccat    1560
catcatcatc atcatggcct gaacgacatc ttcgaggctc agaaaatcga atggcacgaa    1620
tgaaagcttg cggccgcact cgagcaccac caccaccacc actgagatcc ggctgctaac    1680
aaagccc                                                              1687
```

The invention claimed is:

1. A method of screening a functional protein or a functional peptide, comprising:
  (a) disposing a nucleic acid immobilized on a solid support and a cell-free synthesis system in a reactor, in which a reactor array includes the reactor having a specific aperture shape and a protein capture molecule or a peptide capture molecule provided on at least a portion of wall surface and bottom surface in the reactor;
  (b) manufacturing a protein array or a peptide array by synthesizing a protein or a peptide from the nucleic acid using the cell-free synthesis system and immobilizing the protein or the peptide in the reactor; and
  (c) performing a functional screening using the protein array or the peptide array to specify a reactor of the reactor array containing a functional protein or a functional peptide.

2. The method of screening a functional protein or a functional peptide according to claim 1, further comprising:
  (d) recovering, before (c), at least one nucleic acid in the reactor.

3. The method of screening a functional protein or a functional peptide according to claim 2,
  wherein (d) is superimposing a substrate having an affinity to the solid support with the reactor array, thereby printing the nucleic acid on the substrate.

4. The method of screening a functional protein or a functional peptide according to claim 1, further comprising:
  (e) analyzing a base sequence of the nucleic acid corresponding to the reactor specified in the (d).

5. The method of screening a functional protein or a functional peptide according to claim 1,
  wherein the nucleic acid immobilized on the solid support is one type of nucleic acid per solid support.

6. The method of screening a functional protein or a functional peptide according to claim 1,
  wherein one solid support is disposed in one reactor.

7. The method of screening a functional protein or a functional peptide according to claim 1,
  wherein the solid support is a magnetic bead.

8. The method of screening a functional protein or a functional peptide according to claim 1,
  wherein the protein capture molecule or the peptide capture molecule is a molecule having an affinity to an amino acid sequence existing in the protein or the peptide.

9. The method of screening a functional protein or a functional peptide according to claim 1, wherein
  the protein capture molecule or the peptide capture molecule is a nucleic acid linker having a protein linking moiety or a peptide linking moiety, and
  the method further comprises transcribing an mRNA from the DNA using the cell-free synthesis system in the reactor, synthesizing a protein or peptide from the mRNA hybridized to the nucleic acid linker, and immobilizing the protein or peptide in the reactor.

10. The method of screening a functional protein or a functional peptide according to claim 1, further comprising:
  (d) sealing the reactor between the (a) and the (b).

11. A method of screening a functional protein or a functional peptide, comprising:
  (a) disposing a nucleic acid immobilized on a solid support and a cell-free synthesis system in a reactor, in which a reactor array includes the reactor having a specific aperture shape and a puromycin linker comprising a reversible photoligating base and a puromycin derivative as a protein capture molecule or a peptide capture molecule provided on at least a portion of wall surface and bottom surface in the reactor;
  (b) manufacturing a protein array or a peptide array by synthesizing a protein or a peptide from the nucleic acid using the cell-free synthesis system and immobilizing the protein or the peptide in the reactor through the puromycin linker;
  (c) irradiating the puromycin linker with light to cleave the photoligating base, thereby dissociating the nucleic acid from the reactor and collecting the dissociated nucleic acid; and
  (d) performing a functional screening using the protein array or the peptide array to specify a reactor of the reactor array containing a functional protein or a functional peptide.

* * * * *